United States Patent [19]

Burkhardt et al.

[11] 4,144,636
[45] Mar. 20, 1979

[54] METHOD FOR MANUFACTURE OF A MOISTURE SENSOR

[75] Inventors: Paul J. Burkhardt, Poughkeepsie; Michael R. Poponiak, Newburgh, both of N.Y.

[73] Assignee: International Business Machines Corporation, Armonk, N.Y.

[21] Appl. No.: 822,589

[22] Filed: Aug. 8, 1977

Related U.S. Application Data

[62] Division of Ser. No. 701,788, Jul. 2, 1976, Pat. No. 4,057,832.

[51] Int. Cl.$^2$ ............................................. B01J 17/00
[52] U.S. Cl. .................................. 29/590; 29/576 R; 204/15; 204/129.3
[58] Field of Search .......................... 29/576, 589, 590; 204/15, 129.3

[56] References Cited

U.S. PATENT DOCUMENTS 3,835,530  9/1974  Kilbey ..................................... 29/577
3,919,060  11/1975  Pogge ................................ 204/129.3

OTHER PUBLICATIONS

IBM Technical Disclosure, "Dielectric Isolation of Si Devices" by Badami, vol. 18, No. 1, 6/75, pp. 116 & 117.

Primary Examiner—W. Tupman
Attorney, Agent, or Firm—George O. Saile

[57] ABSTRACT

A method and resulting structure for a relative humidity monitor which can be built into an integrated circuit chip. A small area on a silicon chip is made porous by anodic etching. This region is then oxidized and a metal counter electrode is deposited over part of the porous area. The surface area in the dielectric under the counter electrode is very high and because of the openness of the structure, ambient moisture can quickly diffuse into the dielectric under the electrode and adsorb onto the silicon dioxide surface. Changes in ambient humidity will then be reflected by measurable changes in capacitance or conductance of the device.

8 Claims, 19 Drawing Figures

METHOD FOR MANUFACTURE OF A MOISTURE SENSOR

This is a division of application Ser. No. 701,788, filed July 2, 1976, now U.S. Pat. No. 4,057,832 issued Nov. 8, 1977.

BACKGROUND OF THE INVENTION

The invention relates to a miniature humidity or moisture sensing device and more particularly to a device and method for manufacturing the device which may be built into an silicon integrated circuit chip.

DESCRIPTION OF PRIOR ART

Long term device reliability in integrated circuit chips has been shown to be a function of ambient moisture temperature. Other ambients containing corrosive gases have also contributed to reduced reliability and even failure of integrated circuits. The primary reliability problem has been moisture. There have been suggestions to place a moisture sensor inside an encapsulated package having an integrated circuit such as in the publication "Miniature Moisture Sensors for In-Package Use By the Microelectronics Industry" by D. E. Meyer, Apr. 1, 1975, International Reliability Physics Symposium, Las Vagas, Nev. However, no satisfactory sensor has been developed to be used in such a package.

Moisture or humidity sensors currently available are composed of porous layers of electrically conductive materials such as carbon black, U.S. Pat. No. 3,350,941 to K. W. Misevich et al, aluminum oxide, U.S. Pat. No. 3,075,385 to C. M. Stover, and U.S. Pat. No. 3,523,244 to P. Goodman et al, cellulose esters, U.S. Pat. No. 3,582,728 to P. E. Tohms, organosilicon compound, U.S. Pat. No. 3,864,659 to S. Furuuchi et al, an absorbing material such as high silica glass or fused quartz which has been roughened, U.S. Pat. No. 2,976,188, D. A. Kohl, or an N-P junction in semiconductor material, U.S. Pat. No. 2,711,511 to Pietenpol. The problems with these various materials and structures in the aforementioned patents and publications involve either their relatively large size in that they would not be small enough to satisfactorily fit into a package where an integrated circuit is located or the electrical measurement would not be sensitive enough to allow the very accurate measurement of moisture at relatively small amounts so as to predict when the reliability of an integrated circuit is in question prior to the complete failure of that integrated circuit. Neither could any of the proposed devices be successfully integrated within a semiconductor integrated circuit so as to produce the optimum microminiature moisture sensor.

SUMMARY OF THE PRESENT INVENTION

In accordance with the present invention, a method and resulting moisture sensor which is formed in a monocrystalline silicon body. The moisture sensor is a microminiature device which is suitable for placing in an integrated circuit package or is part of the integrated circuit itself. The device is very sensitive to even small amounts of moisture in the ambient. A region in the silicon semiconductor body of high porosity silicon dioxide is made. A metal counter electrode is formed on a part of the porous silicon dioxide region. The porous silicon dioxide has a porosity sufficient that ambient moisture can quickly diffuse into the porous silicon dioxide under the said electrode should the moisture actually be present. The moisture would then be adsorbed onto the silicon dioxide sensor device and cause measurable changes in the moisture sensor device. The counter electrode may be formed so as to produce measurable changes in capacitance or to allow measurable changes in resistance.

The moisture sensor can also form a portion of the integrated circuit chip itself. Where the moisture sensor is integrated into the integrated circuit device, it can be made as a part of the normal fabrication process for such a device. In this instance the size of the moisture sensor is even smaller and takes up even less space in the package in which the integrated circuit device is mounted.

DESCRIPTION OF THE PREFERRED EMBODIMENTS

Figure 1:
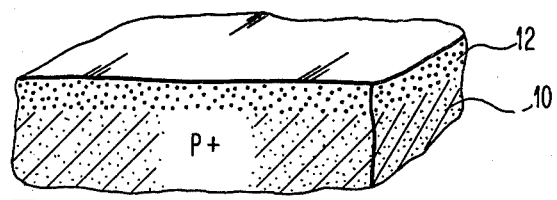
FIGS. 1 and 2 are the initial steps in forming a plurality of discrete moisture sensors of the present invention.

Referring now to FIG. 1, a monocrystalline silicon body 10 which may be for example P+ type and <100> orientation, has its surfaces protected with a layer impervious to HF such as silicon nitride except for the top surface which is left free of any covering. Alternatively, only the top surface can be contacted with the anodizing solution. The silicon body is then anodized in the solution which converts the unprotected silicon to a porous silicon layer 12. This can be conveniently achieved by anodizing the structure in an aqueous hydrofluoric acid solution at a current density sufficient to achieve the desired porosity. The anodizing solution is preferably 10 to 33 percent HF in water. An alternate anodizing solution is described in IBM Technical Disclosure Bulletin, Vol. 18, No. 12, May 1976, pg. 4011. The current density is preferably 0.1 to 20.0 milliamps/cm$^2$. After the anodization step is completed, the average porosity of the porous silicon 12 is in the range of 30 to 80 percent. The most preferable porosity is of the order of 60 percent. Porosity greater than about 80 percent produces mechanically fragile film.

Figure 2:
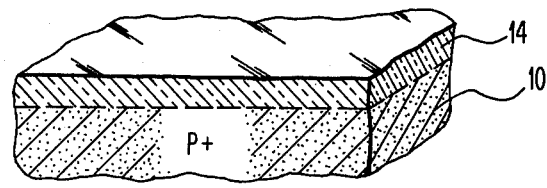

The FIG. 1 structure with the semiconductor monocrystalline silicon body 10 having a silicon porous surface 12 now must be oxidized. Oxidation may be accomplished using a thermal technique which involves placing the silicon body having the porous silicon surface in a thermally oxidizing ambient at a temperature above about 500° C. and preferably below 1200° C. Suitable oxidizing environment is typically oxygen or steam or a combination of both. An alternate oxidizing technique is the use of anodic oxidation at room temperature. A suitable anodic oxidation electrolyte is HNO$_3$ or N-Methylacetamide. The current density is about 6MA/cm$^2$. The result of the oxidizing process is the FIG. 2 structure which is a monocrystalline silicon body 10 having a porous silicon dioxide layer 14.

The operative silicon dioxide porosity is between about 15 to 40 percent. The optimum porosity of the $SiO_2$ layer is approximately 30 to 35 percent. Too dense a film creates a large hysteresis effect due to the trapping of moisture in the pores. The uniqueness of this porous layer is its configuration of vertical and horizontal pores following the crystallographic orientation of the <100> silicon body. This structure facilitates the movement of moisture.

Figure 3:
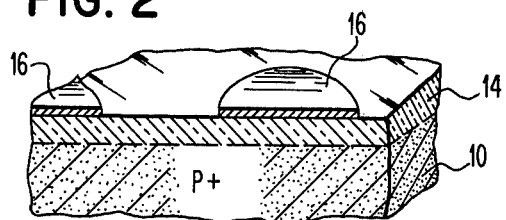
FIGS. 3 and 4 illustrate fabrication of a moisture sensor which provides measurable changes in capacitance or resistance when moisture is present.
Figure 3A:
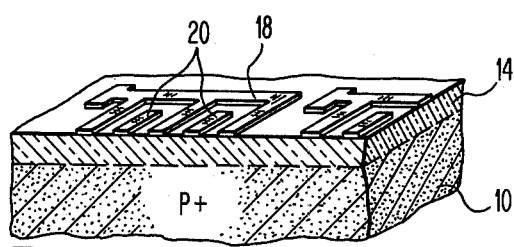
FIGS. 3A and 4A illustrate alternate resulting structures in the fabrication of a moisture sensor where measurable changes in capacitance or resistance are produced when there is moisture present.

The next steps in forming a moisture sensor may be understood with the aid of FIGS. 3 and 3A. A suitable metal counter electrode is deposited by vacuum deposition through an appropriate mask such as a metal mask or a photoresist mask formed in the conventional photolithography techniques. The photoresist type mask defines a more accurate pattern because it adheres to the surface as opposed to a metal mask which does not adhere to the surface. The FIG. 3 structure shows a counter electrode 16 on the surface of the porous silicon dioxide region 14 which is usable to measure changes in capacitance or resistance. The FIG. 3A alternative shows the metal counter electrode composed of two spaced, but interleaved serpentine patterns 18 and 20 on the surface of the porous silicon dioxide region 14. This type structure has a faster response and is more sensitive to changes in capacitance or resistance. Various metals may be utilized for these electrodes. Examples of the metals which are very useful include aluminum, chromium and platinum.

The moisture sensor devices are then diced into discrete devices from the processed wafer. This dicing may be accomplished by conventional scribing and breaking, ultrasonic cutting, etching techniques or other conventional methods. The diced chips are cleaned in suitable solvents and are then ready for mounting in a suitable package.

Figure 4:
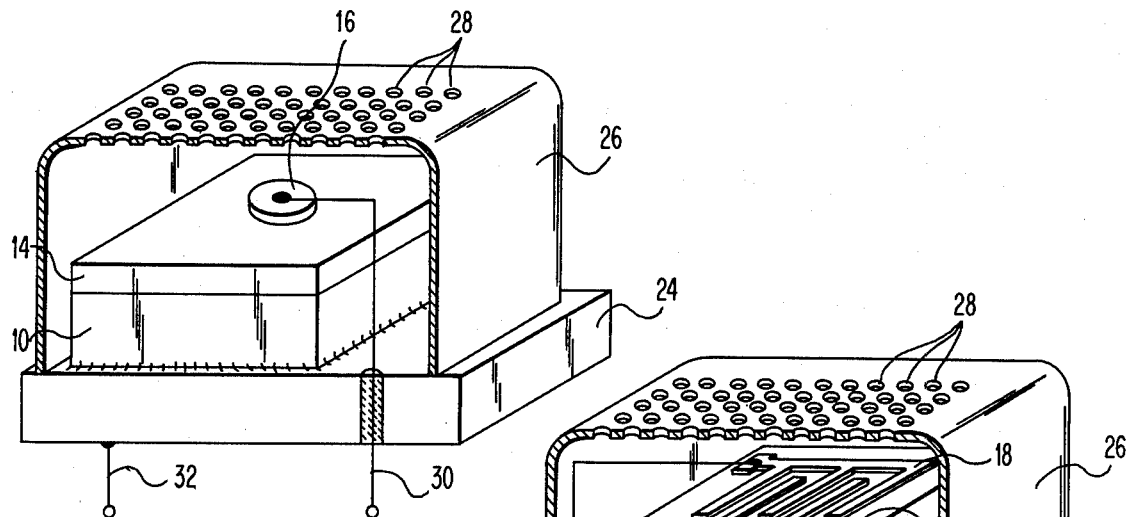
Figure 4A:
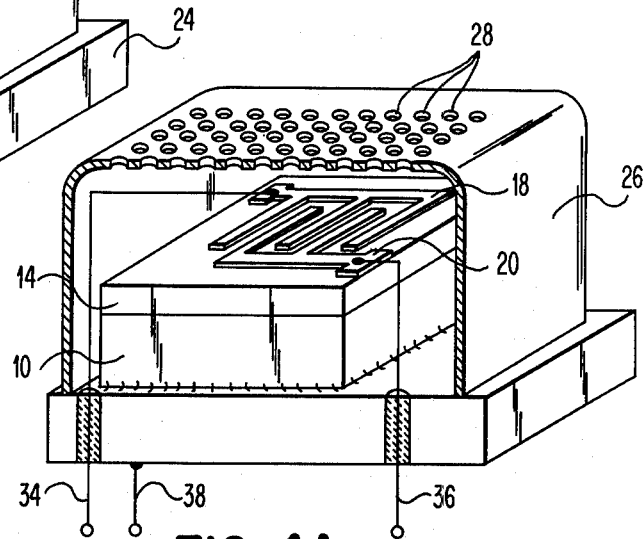

FIGS. 4 and 4A show one suitable package or header for mounting the present moisture sensor. The moisture sensor device of FIG. 3 is packaged in header arrangement of FIG. 4 and the moisture sensor device chip is packaged in the FIG. 4A package. In each case the moisture sensor chip is soldered to the header base 24 and wires bonded by a conventional ultrasonic bonding technique. A cover 26 having a plurality of openings 28 above the porous silicon region 14 is attached to the header base 24. The cover may be formed of any suitable metal or plastic since the primary function is to prevent mechanical damage to the semiconductor moisture sensor chip. The holes 28 allow the moisture from the ambient to contact the porous silicon dioxide region and where moisture is present it is adsorbed into the region underneath the metal electrode 16 in the case of FIG. 4 and the metal electrodes 18 and 20 in the case of FIG. 4A. The capacitor contact 16 is contacted electrically with a suitable wire 30 which extends through the header base 24 which is grounded by wire 32. Measurable changes in capacitance or resistance may be obtained across these contacts using a suitable electric meter such as a Boonton capacitance meter or Keithley electrometer.

In the case of the capacitance or resistance measuring device of FIG. 4A, the electric wires are attached to the serpentine patterns 34 and 36 which are extended through the base 24 and a ground wire 38 is attached to the base. Measurable capacitance or resistance changes are made using an appropriate meter and measuring across contacts 34 and 36 or shunting 34 and 36 and measuring between them and 38.

Referring to FIGS. 5-12, there is shown a method for forming a preferred integrated circuit and moisture sensor structure. U.S. Pat. No. 3,919,060, issued Nov. 11, 1975 to H. B. Pogge et al and assigned to the same assignee as the present invention, describes methods for forming dielectrically isolated silicon regions in integrated circuits. Reference may be made to that patent for details of forming integrated circuits. The silicon substrate 40 was masked with a suitable layer and openings made therein to form an N+ type doped region 42 and a P+ doped regions 44 and a large P+ region 46. This masking layer is then removed and epitaxial silicon layer 48 of an N type grown on the surface of the substrate 40. During the growth of the epitaxial layer there is out diffusion from the diffused regions 42, 44, 46 into the epitaxial layer as indicated in the FIG. 5.

A masking layer of silicon dioxide 50 is applied or grown and a pattern etched therein using conventional photolithography and etching techniques to find a grid of openings that will overlie the P+ regions 44 and 46 in the substrate 40. A further pattern of openings in the mask may be made over the region 42 which will ultimately separate the base-emitter region from the collector contact region. This is an optional feature.

Figure 5:
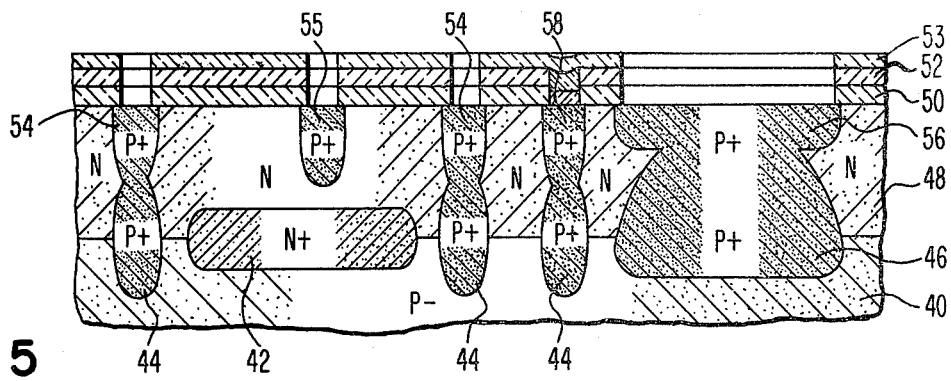
FIGS. 5–12 illustrate one form for the manufacture of an integrated moisture sensor.

A conventional diffusion or ion implantation step then results in a grid of high conductivity P+ type regions 54, 55, 56 and 58. The 54 regions contact the upper portion of the 44 region to make a P+ region surrounding the areas which are to be bipolar devices. The 55 region approaches the N+ subcollector region 42 and separates what will be the emitter-base region from the collector reachthrough. The large 56 region contacts the large 46 P+ region which will ultimately be the moisture sensor device. The 58 region contacts a 44 region adjacent to the moisture sensor to form a pillar of P+. The structure of FIG. 5 is re-oxidized producing a continuous layer 50. A $Si_3N_4$ layer 52 and pyrolytic $SiO_2$ layer 53 is deposited and open to surface of diffused region 54, 55, 56 accomplished by standard photoresist techniques. Layer 53 is removed in the HF anodization electrolyte during anodization.

Figure 6:
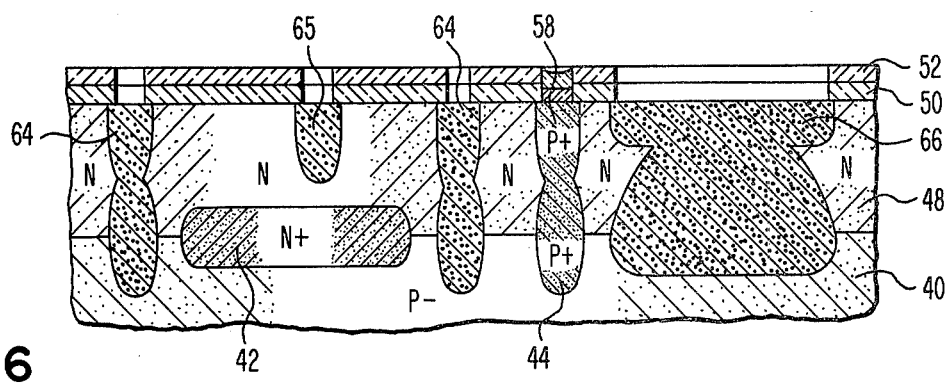

The resulting structure of FIG. 5 is exposed to an anodization step as described in relation to FIG. 1 above. The result is the conversion of regions 44, 54 to the porous silicon region 64, the region 55 to porous silicon region 65, the regions 46, 56 to the porous region 66. The structure is shown in FIG. 6.

Figure 7:
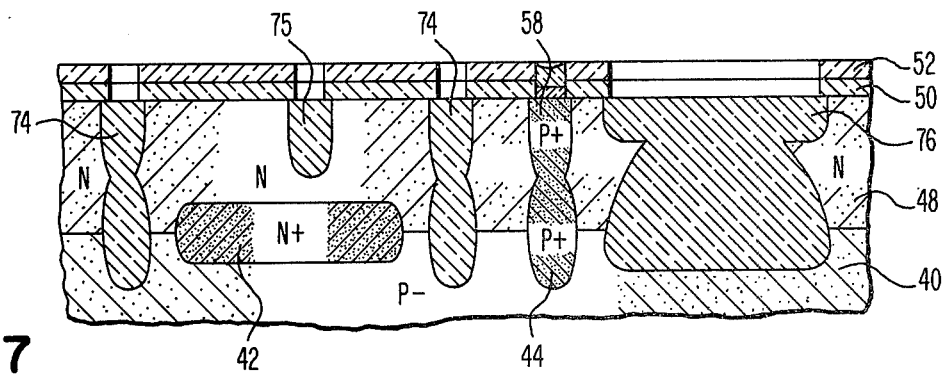
Figure 8:
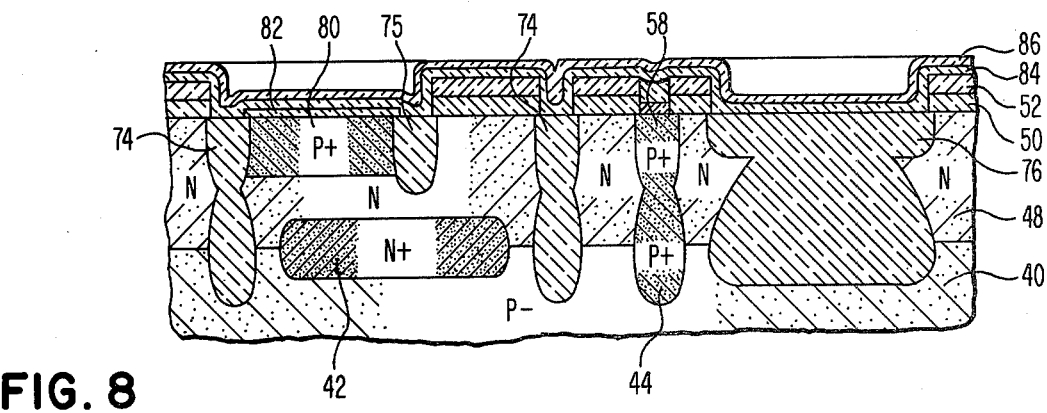
Figure 9:
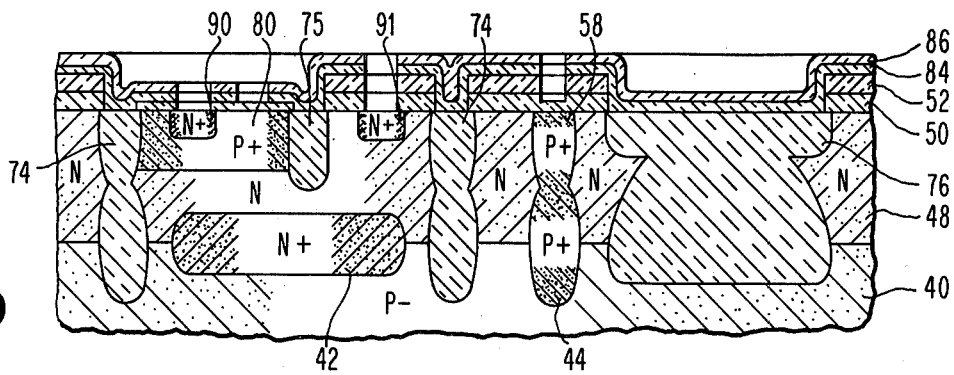

As indicated in FIG. 7, the porous silicon regions 64, 65 and 66 are oxidized in a suitable oxidizing ambient to form the porous silicon dioxide regions 74, 75 and 76. This oxidation is similar to that described with reference to FIG. 2 above.

Various types of semiconductor devices, both active and passive can be formed by any of a variety of semiconductor processing techniques into the isolated pockets such as isolated by dielectric isolation regions 74. In the embodiment shown, beginning with FIG. 8, a standard bipolar transistor is formed in that pocket defined by the porous oxide region 74. An opening is made in the silicon dioxide silicon nitride layers 50 and 52 in the region that is to be the base region of the bipolar device and a P+ diffusion is made through these openings to form the base region 80. Reoxidation is then accomplished using standard oxidation techniques to form the oxide layer 82. Layers of silicon nitride 84 and silicon dioxide 86 are deposited by chemical vapor deposition over the entire surface to produce the structure of FIG. 8.

Figure 10:
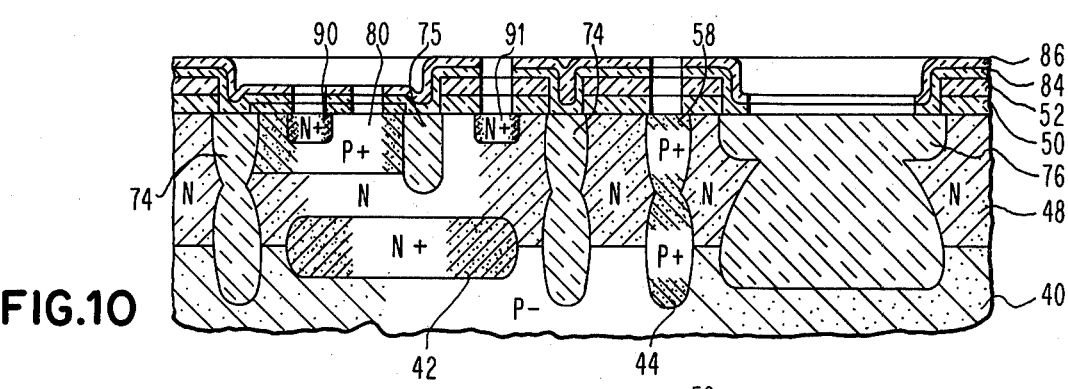

Openings are made for the emitter and collector contact diffusion. The diffusion of an N+ impurity is then made by either diffusion or ion implantation techniques to produce the emitter region 90 and the collector contact region 91. Openings are then made for the emitter-base, collector, and substrate reachthrough and the moisture sensor device as shown in FIG. 10 by suitable photolithography and etching techniques.

Figure 11:
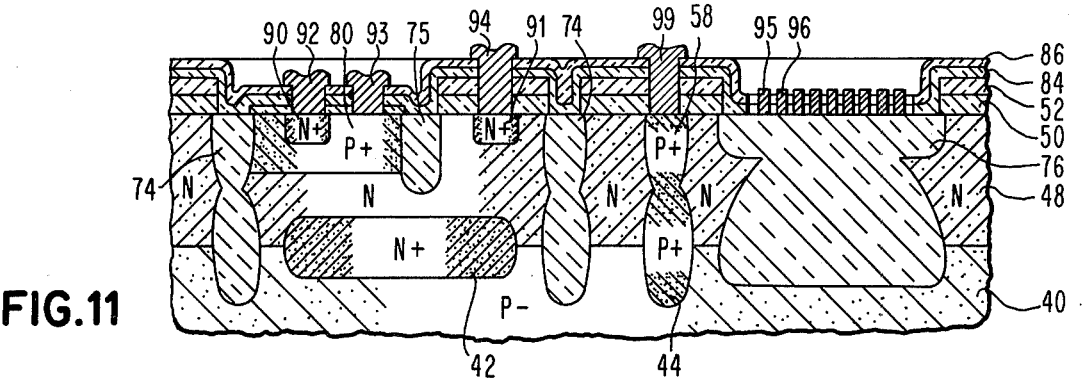
Figure 12:
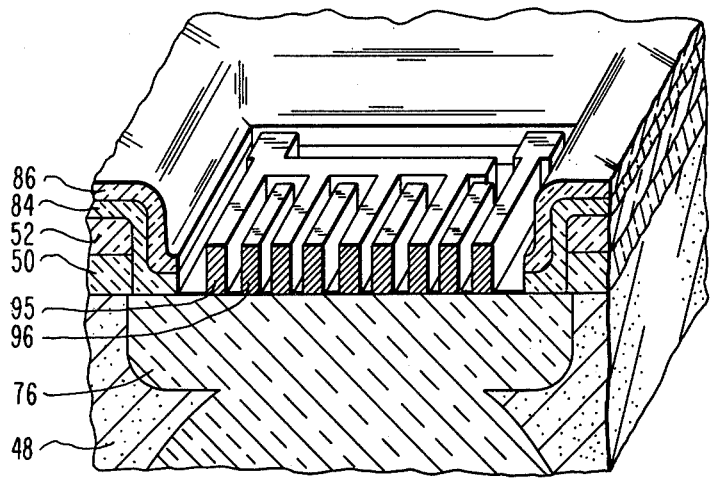
Figure 13:
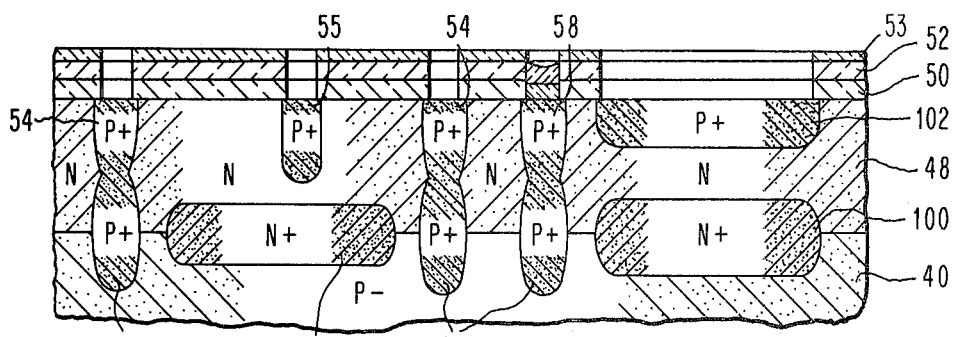
FIGS. 13–16 show another form for the fabrication of an integrated moisture sensor device.
Figure 14:
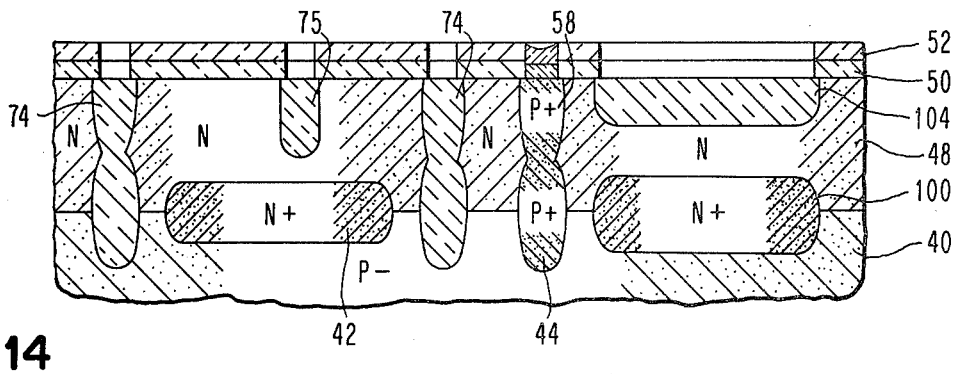
Figure 15:
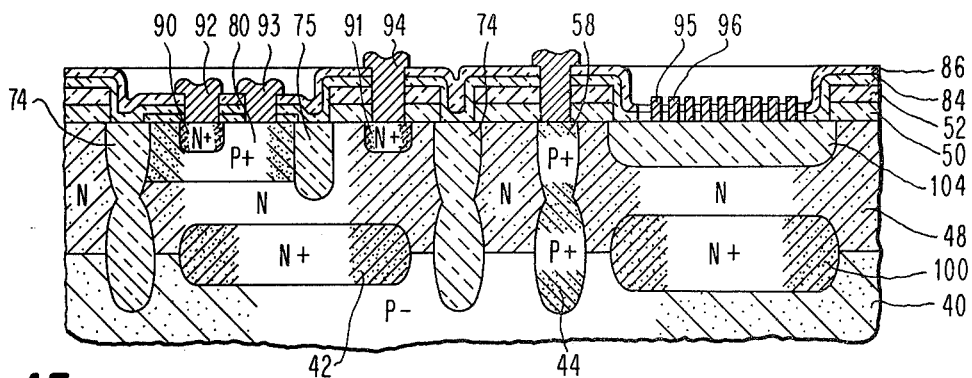
Figure 16:
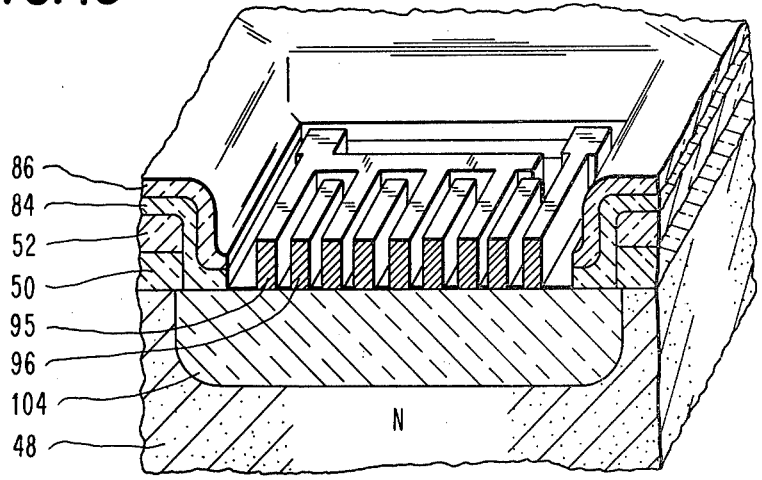

Suitable electrical contacts are then formed to the emitter, base and collector of the bipolar device and also the substrate reachthrough. Emitter contact is 92, base contact 93, collector contact 94, and substrate reachthrough 99. The metallurgy may be deposited by conventional blanket diffusion of a metal, such as aluminum, over the entire surface followed by the use of standard photolithographic and etching techniques to form the desired contact. The metallurgy for contact for the moisture detector shown in FIG. 11 is two spaced, but interleaved serpentine patterns 95 and 96. The structure is shown in perspective in FIG. 12. This structure will then be mounted into a suitable package similar to that shown in FIGS. 4 and 4A. The moisture sensor would then act to register changes in resistance or capacitance due to moisture adsorbed on the silicon dioxide under the contact 95, 96.

The embodiment shown in FIGS. 13-16 is a modification of the FIGS. 5-12 process and resulting integrated circuit moisture sensor device. Like numbers in these FIGS. 13-16 to the FIGS. 5-12 indicate like structures. The process of FIG. 5 is repeated just prior to structures shown in FIG. 13 except that the region 46 in the substrate 40 which in the case of FIG. 5 of the embodiment of FIGS. 5-12 forms a portion of the porous silicon region of the moisture sensor and is therefore required to be a P+ region is an N+ region 100 in the case of FIG. 13. The P+ diffusion 102 resulting in the structure of FIG. 13 does not extend to the N+ region but is spaced therefrom. The procedures described in the FIGS. 5-12 embodiment which includes the oxidation and formation of the porous silicon dioxide, the fabrication of the integrated circuit structure as shown with the bipolar device example, the deposition of metallurgy to form the contacts to the integrated circuit device as well as a serpentine metallurgy structure on the moisture sensor device to measure changes in resistance in the porous silicon dioxide are the same in FIGS. 13-16 embodiment. Figures showing these steps have not been repeated. Only the preporous silicon step structure in FIG. 13, the post formation of porous silicon dioxide structure in FIG. 14 and the resulting structures of FIG. 15 and FIG. 16 of the entire process are included and believed to be sufficient explanation to understand that embodiment.

The following Example is included merely to aid in the understanding of the invention and variations may be made by one skilled in the art without departing from the spirit and scope of the invention.

EXAMPLE

A P+ <100> silicon wafer having a resistivity of 0.01 ohm-centimeter had its top surface made porous to the depth of 2½ microns by anodic dissolution at a current density of 10 milliamperes/cm$^2$ for seven minutes. Only the wafer's top surface contacted the anodic dissolution. The electrolyte consisted of 0.5 percent HF in concentrated (37%) hydrochloric acid. The resultant layer had a porosity of 79%. The porous silicon layer was then oxidized in dry oxygen at 1025° C. for 20 minutes to produce porous silicon dioxide with about a 39% porosity. Counter electrodes of 60 mil in diameter were evaporated onto the porous silicon oxide layer by conventional contact mask and aluminum evaporation. The wafers were then diced into individual devices and mounted onto T105 headers. A gold wire was ultrasonically bonded onto the aluminum dot to make connection to the header stud. Five holes were pierced through the header cover. The cover was then attached to the substrate to complete the device.

Figure 17:
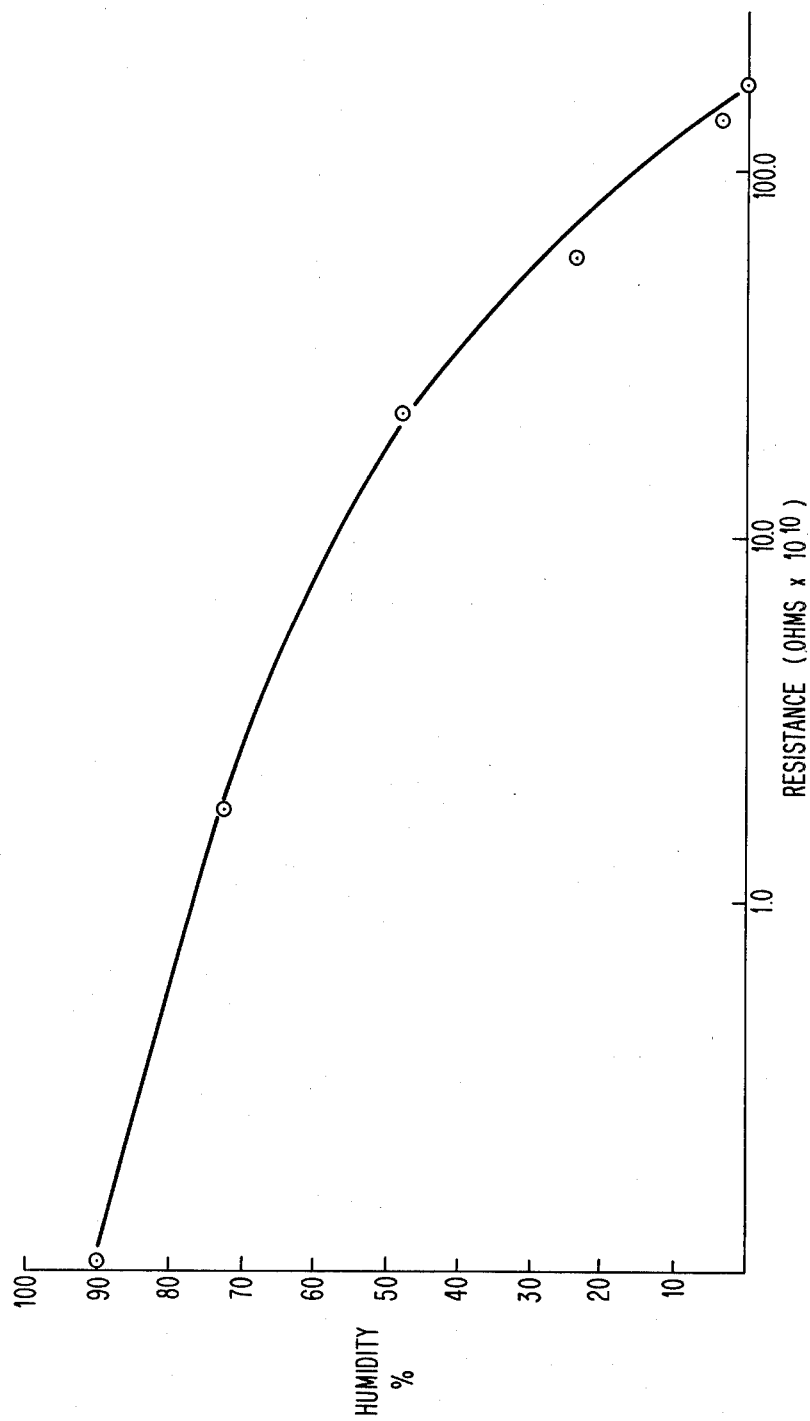
FIG. 17 gives the effect of different levels of moisture upon the resistance of moisture sensors in the Example.

The moisture sensor devices were mounted in the lids of jars containing constant humidity from a sulfuric acid-water solution giving relative humidities ranging from 3.9% to 90%. The sulfuric acid solutions were prepared by mixing predetermined amounts of concentrated sulfuric acid with deionized water, allowing the solution to cool to room temperature, then measuring specific gravity with a float hydrometer. Tables of relative humidity and specific gravity for sulfuric-water solutions are given in standard handbooks of Chemistry and Physics. The devices were subjected to various relative humidities for a period of several minutes and the resistances were measured with a Keithley Model 616 Digital Electrometer. The following Table gives the relative humidity versus the resistance in ohms. FIG. 17 is a plot of this relative humidity versus resistance in ohms × $10^{10}$.

TABLE

| | R in ohms | |
|---|---|---|
| 0% | 170 × $10^{10}$ | (dry $N_2$ standard) |
| 3.9% | 140 × $10^{10}$ | |
| 24% | 58 × $10^{10}$ | |
| 48% | 22 × $10^{10}$ | |
| 72% | 1.75 × $10^{10}$ | |
| 90% | .1 × $10^{10}$ | |

While the invention has been particularly shown and described with reference to preferred embodiments thereof, it will be understood by those skilled in the art that the foregoing and other changes in form and details may be made without departing from the spirit and scope of the invention.

What is claimed is:

1. The method for producing a moisture sensor comprising:
   anodizing a region of a monocrystalline silicon body to form a porous silicon layer having an average porosity of 30 to 80 percent;
   oxidizing the surface of said porous silicon layer to form a porous silicon dioxide layer having an average porosity of 15 to 40 percent; and
   forming a plurality of spaced apart electrodes onto said sensor and wherein at least one of which is connected to the said porous silicon dioxide layer so as to allow the detection of electrical measurable changes due to adsorption of moisture in said porous silicon dioxide layer.

2. The method of claim 1 wherein the porous silicon layer is formed in a 10 to 33 percent concentrated HF-water solution at from about 0.1 to 20 milliamps/cm$^2$.

3. The method of claim 1 wherein the porous silicon dioxide layer is formed by thermal oxidation at a temperature greater than about 500° C.

4. The method of claim 1 wherein the porous silicon dioxide layer is formed by anodization.

5. The method of claim 1 wherein the porous silicon layer is formed in about 0.5 to 26 percent HF in HCl water solution at from about 0.1 to 20 milliamps/cm$^2$.

6. The method of claim 1 wherein said electrodes include an electrode on said silicon body which allows measurable changes in capacitance.

7. The method of claim 1 wherein said electrodes include two spaced but interleaved serpentine patterns connected to said porous silicon dioxide layer so as to allow measurable changes in resistance.

8. The method of claim 1 wherein an integrated circuit is formed in said monocrystalline silicon body.

* * * * *